(12) United States Patent
DeMarcki

(10) Patent No.: US 6,656,434 B1
(45) Date of Patent: Dec. 2, 2003

(54) COMPACT PORTABLE OWNER-SERVICED AIR DUCT SANITIZING SYSTEM

(76) Inventor: Robert Bancker DeMarcki, 3554-65th Ave. Cir., E. Sarasota, FL (US) 34243

( * ) Notice: Subject to any disclaimer, the term of this patent is extended or adjusted under 35 U.S.C. 154(b) by 447 days.

(21) Appl. No.: 09/649,417

(22) Filed: Aug. 26, 2000

(51) Int. Cl.[7] ................................................. A62B 7/08
(52) U.S. Cl. ..................... 422/120; 422/116; 422/123; 422/124
(58) Field of Search ................. 422/120, 123, 422/124, 116

(56) References Cited

U.S. PATENT DOCUMENTS

| | | | | |
|---|---|---|---|---|
| 3,591,328 A | * | 7/1971 | Szappanyos et al. | 427/236 |
| 4,601,886 A | * | 7/1986 | Hudgins | 422/116 |
| 4,780,333 A | * | 10/1988 | Smith et al. | 427/236 |
| 5,281,401 A | | 1/1994 | Bryson, Sr. | |
| 5,549,247 A | * | 8/1996 | Rossman et al. | 239/57 |
| 5,664,423 A | * | 9/1997 | Akazawa | 62/78 |
| 5,833,929 A | * | 11/1998 | Watson et al. | 422/123 |
| 5,911,742 A | * | 6/1999 | Akazawa | 62/78 |
| 5,957,771 A | * | 9/1999 | Baek | 454/233 |
| 6,032,930 A | * | 3/2000 | Calino | 261/26 |

* cited by examiner

Primary Examiner—Krisanne Thornton
(74) Attorney, Agent, or Firm—Dorothy S. Morse

(57) ABSTRACT

A compact, portable, and user-friendly duct sanitizing apparatus and method, for new construction and retrofitting to existing air conditioning and heating systems, which can be professionally or nonprofessionally installed and then easily serviced by a non-professional. The present invention has a housing supporting a refillable non-pressurized fluid reservoir; 24-volt electric pump capable of producing 60 psi fluid pressure; at least one nozzle capable of producing a 250μ mist connected to the main plenum and each associated air duct; fluid carrying tubing rated at 200 psi connected between the pump and each misting nozzle; fully-automated 24-volt programmable timer with power loss backup; recycle timer; rectifier; fan relay to by-pass the air conditioning or heating system thermostat when its fan is inactive and needed to assist with mist dispersal; and electrical wiring between the programmable timer and the air conditioning or heating system for use in providing low voltage power to the sanitizing apparatus. Optionally, the electrical components can be attached to a mounting board removably fixed within the housing to facilitate manufacture and maintenance. Over time the 250μ mist, preferably chlorine dioxide, will coat the interior of the air ducts to kill bacteria, viruses, yeast, fungi, algae, molds, and mildew, and thereafter maintain them in a sanitized condition. Since each housing is optimally connected to a maximum of approximately six misting nozzles, some buildings will require more than one sanitizing apparatus. In addition to air duct sanitation, the present invention can be easily adapted for air purification and aromatherapy applications.

15 Claims, 3 Drawing Sheets

COMPACT PORTABLE OWNER-SERVICED AIR DUCT SANITIZING SYSTEM

BACKGROUND

1. Field of Invention

This invention relates to devices used for sanitizing air conditioning and heating system ducts, specifically to a compact user-friendly, portable air duct sanitizing apparatus and method, for new construction as well as retrofitting to existing air conditioning and heating systems in commercial and residential buildings, which can be either professionally or owner installed, with routine maintenance thereafter being easily and safely performed by the owner or other non-professional. The sanitizing apparatus of the present invention comprises a system control unit with a housing that supports a refillable non-pressurized reservoir of liquid sanitizing agent, which is removably attached to the housing without opening the housing cover. In addition the housing supports and protects a 24-volt electric pump capable of moving fluid through tubing at a pressure of approximately 60 psi and a fully automated 24-volt programmable timer with power loss backup. The sanitizing apparatus also comprises a plurality of misting nozzles each capable of creating a fine mist having droplets with a maximum diameter dimension of approximately 250μ. Each misting nozzle is connected via tubing between the pump and one of the air ducts targeted for sanitizing, with at least one misting nozzle being inserted into each of the air ducts, as well as into the main plenum to which the air ducts are connected. When more than one air duct is targeted for sanitizing, the misting nozzles are connected to a branching array of fluid carrying tubing rated to withstand a maximum pressure of approximately 200 psi that has a trunk line connected to a single hose fitting on the pump. The pump in each system control unit housing is selected to provide liquid sanitizing agent to a maximum of approximately six air ducts. In addition, the present invention also comprises electrical connection means between the 24-volt programmable timer and the air handler of the air conditioning or heating system with which it is associated that allows the sanitizing apparatus to be internally powered through the associated air conditioning or heating system. The system control unit housing of the present invention is preferably mounted in commercial or residential structures in a location remote from the air conditioning ducts, where it can be easily accessed for timer reprogramming and fluid reservoir exchange or refill. The fine mist entering the air ducts is evenly dispersed therein by the fan of the associated air conditioning or heating system, to coat the inside of the air ducts so as to kill bacteria, viruses, fungi, yeast, algae, molds, and mildew over a period of time and thereafter maintain the air ducts in a sanitized condition. As a result, the air duct sanitizing apparatus of the present invention also comprises a fan relay to by-pass the air conditioning or heating system thermostat during such time when the fan is not in an operating mode and it is needed to assist in mist dispersal. Optional use of a planar polyvinyl chloride (PVC) mounting board for electrical components that is removable from the housing not only facilitates manufacture by making it easier for the people assembling the present invention to connect the wiring between electrical components, it also facilitates servicing and replacement of electrical components since the mounting board is easily releasable from the installed housing, typically by unfastening the nuts respectively attached to two bolts. Safety features of the present invention include the high-pressure rated tubing, the reduced voltage timer and pump, a pump that safely operates wet or dry should the operator fail to anticipate timely replacement or refill of the reservoir before all of the fluid therein is completely used, the pump also having a fluid loop should the fluid discharge opening of the pump become inadvertently blocked, and the non-pressurized supply of low toxicity non-flammable sanitizing agent. Although not limited thereto, chlorine dioxide is the sanitizing agent preferred for use with the present invention, as it has a low toxicity and a category III EPA safety rating. In addition to air duct sanitizing, the present invention can also be used for air purification and aromatherapy.

2. Description of Prior Art

The interior walls of the air ducts of ventilation systems are subject over time to the accumulation of particulate matter, as well as the growth of algae, yeast, fungi, bacteria, molds, and mildew. Also, the air drawn through such ducts may contain bacteria and viruses that are so small in size they cannot be removed by filtration. As a result, the continued recycling of air with no conditioning other than filtration can lead to high levels of allergens and other contaminants in ventilation system ducts that can cause those sensitive to them to experience discomfort and/or become ill. Systems to sanitize and condition air in ventilation systems are known. However, most are expensive and/or require professional installation, maintenance, or both. The present invention comprises an air duct sanitizing, de-odorizing, conditioning, and purification system that is user-friendly and has a compactly configured lightweight system control unit housing that can be installed by a non-professional in any location convenient for easy maintenance access. The present invention also has built-in safety features that allow essentially risk-free routine owner maintenance and use. Further, through simple exchange of the non-pressurized fluid reservoir for one containing a different chemical solution, and easy adjustments made to the programmable timer, alternative uses of the present invention can include aromatherapy and air purification.

The invention thought to be the closest in concept to the present invention is the invention disclosed in U.S. Pat. No. 5,281,401 to Bryson, Sr. (1994). However, many important differences exist between the Bryson, Sr. invention and the present invention. The Bryson, Sr. invention comprises a container with a one-way valve for permitting the inflow of air into the container, a pressurized cartridge positioned within the container and adapted for dispensing a vapor into the container, an intermittently operable air and vapor pump, a timer for intermittent activation of the pump with the periods of operation and non-operation being independently variable, and conduit for conveying the air and vapor mixture between the container and the pump, as well as between the pump and an air duct. When multiple segments of conduit are joined, the Bryson, Sr. invention contemplates the use of a valve to adjust the vapor flow into various portions of the conduit. Also, in the Bryson, Sr. invention two independent timers are preferred, one to control the operation time and the other to control the non-operation time. The control box for the Bryson, Sr. invention may be attached directly to the outside surface of an air duct, or in the alternative situated remotely from the duct into which the Bryson, Sr. invention directs its air and vapor mixture. Also, a power supply cord in the Bryson, Sr. invention electrically connects the pump and timer to a standard electrical outlet. As the liquid in the cartridge is spent, the amount of vapor in the canister after a period of rest will become reduced. As a result, timer adjustment is required in the Bryson, Sr. invention when the cartridge fluid level is reduced to allow for more uniform distribution of the vapor. In contrast, the present invention comprises a fully automated 24-volt programmable timer with power loss backup, a non-pressurized reservoir of liquid sanitizing agent which can be refilled or replaced by a new reservoir having the same or different liquid sanitizing or aromatherapy agent, a plurality of nozzles each capable of creating a mist of droplets having a maximum diameter dimension of approximately 250µ with at least one of the nozzles being inserted into each of the air ducts targeted for sanitizing and at least one nozzle being inserted into the main plenum to which the air ducts are connected, each nozzle being attached on the distal end of a segment of fluid carrying tubing rated at approximately 200 psi that is connected between the pump and the air duct or main plenum, and electrical connection means between the 24-volt programmable timer and the air handler of the air conditioning or heating system that allows the sanitizing apparatus to be internally powered thereby at reduced voltage without the limitation of having to position the system control unit housing near to an electrical outlet or the further expense of a step-down transformer to convert municipally provided higher voltage electricity to the lower 24-volt alternating current required for safe non-professional operator use. The pump of the present invention is optimally used with no more than a maximum of approximately six misting nozzles for uniform and effective mist coating of air duct interior surfaces. The present invention has no mixing chamber for air and vapor similar to the Bryson, Sr. invention, and no one-way valve to draw air into a vapor-filled chamber which when subjected to vacuum pressure creates an air and vapor mixture that is then circulated by a pump through conduit for dispensing into the atmosphere of an air duct. Instead, the present invention pump is used to draw sanitizing liquid through various branching segments of tubing each ending in a misting nozzle. The mist is only created as the liquid is forced through the nozzles. Thus, since there is no vapor in the fluid reservoir and it is not a mixing chamber, no timer adjustment is required to maintain a threshold level of vapor in the fluid reservoir for mixing and distribution as the sanitizing agent is consumed. Further, a fan relay is used to by-pass the thermostat of the air conditioning or heating system with which the present invention is associated to activate its fan when the fan is not already in an operational mode so that the fan can run concurrently with the pump and be used to disperse the 250$\mu$ or smaller mist droplets evenly throughout the air ducts. In addition to the fan relay, the present invention also comprises a full bridge rectifier that is not disclosed in the Bryson, Sr. invention. The pump of the present invention is also adapted to operate safely wet or dry should the owner forget to exchange or refill the removable reservoir before all of the sanitizing fluid therein is completely used. Also, for operator safety and to avoid pump failure, the pump has a fluid by-pass loop in the event that its discharge opening becomes inoperable for any reason, and the electrical components may optionally be attached to a planar mounting board releasable from the system control unit housing for ease in manufacture as well as servicing convenience. No air duct sanitizing systems are known that have all of the advantages offered by the present invention.

SUMMARY OF INVENTION—OBJECTS AND ADVANTAGES

The primary object of this invention is to provide an air duct sanitizing system that safely and thoroughly kills bacteria, viruses, algae, fungi, yeast, mold, and mildew with continued use in both residential and commercial buildings.

It is a further object of this invention to provide an air duct sanitizing system that is lightweight and compact in configuration with components selected for safe and easy installation, operation, and maintenance by professionals as well as non-professionals. It is also an object of this invention to provide an air duct sanitizing system that is user-friendly and reliable, requiring minimal operator maintenance or attention after initial installation. A further object of this invention is to provide an air duct sanitizing system that is effectively used in new construction, and can also be easily retrofitted to the air ducts in existing air conditioning and heating systems. It is also an object of this invention to provide an air duct sanitizing system with a system control unit that has only reduced voltage electrical connections to enhance the safety of non-professional operators. It is also an object of this invention to provide an air duct sanitizing system that can be quickly converted for aromatherapy applications, as well as air purification applications wherein the chemicals used require temporary building evacuation and a cure period.

As described herein, properly manufactured and used, the present invention would provide an air duct sanitizing system and method for the safe and thorough killing of bacteria, viruses, algae, fungi, yeasts, mold, and mildew with continued use, and could alternatively be put to aromatherapy or air purification use. Liquids approved by the U.S. Environmental Protection Agency for air duct sanitizing purposes, such as but not limited to low toxicity non-flammable chlorine dioxide, would be periodically dispensed by the present invention into the air ducts of populated buildings and dispersed by the fan of the air conditioning or heating system with which the present invention is associated so that the mist droplets of chlorine dioxide evenly coat the interior surfaces of the air ducts targeted for sanitization. Once the present invention was installed either professionally or by the owner, the professional operator, building owner, or other non-professional maintenance personnel could easily maintain its function by periodically refilling the fluid reservoir or simply exchanging an empty reservoir for a new one. Due to its low category III safety rating, when chlorine dioxide is used as the sanitizing agent for the present invention, discarded fluid reservoirs would not require any special handling or disposal. In the alternative, when air purification is required, it could be accomplished by simple exchange of the removable fluid reservoir for one providing the appropriate air purification chemical, temporary evacuation of occupants from the building, and continued circulation of the air purification mist through the air ducts and building for a predetermined period of time, followed by a cure period sufficient to allow dissipation of chemicals to the safe level required for renewed human occupancy. The same quick conversion of the present invention into an aromatherapy system can be achieved by simple exchange of a fluid reservoir filled with sanitizing agent and replacement with a fluid reservoir providing the appropriate non-pressurized aromatherapy liquid, as well as easily performed timer adjustment, if required. In the alternative, pleasing scents can be added to the air duct sanitizing agent to achieve aromatherapy objectives. While the present invention is suitable for new construction, it can also be easily retrofitted to existing air conditioning and heating systems since it comprises a compact pre-assembled system control unit and an easily constructed branching array of fluid carrying tubing that contains a misting nozzle within each of its distal ends so that a mist having droplets with a maximum diameter dimension of approximately 250$\mu$ is directly injected into the main plenum, as well as into each individual air duct connected to the main plenum. The nozzle-duct connections are purposefully made close to the main plenum to best achieve a thorough coating of mist on all interior surfaces of each air duct. The tubing can be made into a variety of suitable branching configurations through the use of T-shaped hose connectors. Electrical outlet access is not a concern in positioning the sanitizing system control unit housing, since a direct electrical connection is made between the air handler of the associated air conditioning system and the sanitizing system control components that allows the present invention to be internally powered through the associated air conditioning or heating system. Such internal power connection also reduces the cost of the system control unit as it eliminates the need for a step-down transformer to provide the 24-volt reduced level of power desired within the system control unit for operator safety. Should a building have multiple air conditioning or heating zones to manage airflow, it is contemplated for one of the present invention air duct sanitizing systems to be used in association with each zone. The system control unit housings used in each zone could then be consolidated in one location for efficient maintenance, or in the alternative they could be located independently from one another, as dictated by available space or as otherwise desired. The sanitizing system control unit housings are lightweight and compact, and therefore easily mounted to most surfaces. Also, since they are made from plastic, such as polypropylene, they are virtually maintenance-free and resistant to the corrosive nature of some of the chemicals used to sanitize air ducts. Connection of the misting nozzles to the air ducts can be easily accomplished by a non-professional since the only steps required are the formation of a pilot hole in the air duct and the application of sealant around the misting nozzle once it is inserted through the pilot hole and in the desired position of use. The present invention can also be safely operated and maintained by a non-professional since routine maintenance is often as simple as the exchange of an empty non-pressurized fluid reservoir for a full one, and occasional adjustments to the programmable timer that may be needed when the present invention is used for a new application. The misting nozzles would preferably be made from stainless steel wrapped in brass so that they would never clog and never wear out, to assist in keeping operator maintenance to a minimum. Also, all of the electrical components within the sanitizing system control unit housing operate on 24-volt power, reducing the risk of shock hazard to any operator needing to open the housing cover and work within the interior of the housing. Safety features of the present invention also include fluid carrying tubing that has a pressure rating approximately three times that used during routine operation to prevent tubing failure in places inconvenient for access by non-professional maintenance personnel, a pump that safely operates wet or dry to guard against pump failure due to operator error in anticipating the need for reservoir refill or exchange, and the pump having a fluid recycle loop to prevent pump failure and/or operator injury in the event that the pump discharge opening should become blocked or otherwise inoperative. Further, the amount of operator maintenance is also reduced by the fully automated programmable timer of the present invention having a power loss backup, so that reprogramming of the timer is not required every time the electricity fails for a short period of time. Also, ease of manufacture and operator convenience are enhanced when the electrical components in the system control unit housing of the present invention are attached to a mounting board secured within the housing by a minimum number of fasteners. Optional use of a planar polyvinyl chloride (PVC) mounting board for electrical components that is removable from the housing not only facilitates manufacture by making it easier for the person assembling the present invention to attach the wiring between electrical components, it also facilitates servicing and replacement of electrical components since the mounting board is easily releasable from the installed housing. Since the present invention uses a plurality of nozzles that produce a mist with droplets having a maximum diameter dimension of approximately $250\mu$, and also has a fan relay that by-passes the air conditioning or heating system thermostat for prompt activation of the fan in the air conditioning or heating system associated with the present invention when the fan is not already in an operational mode so that the fan can be used for more thorough and even dispersal of the mist within the main plenum and attached air ducts, the present invention would be expected to have consistent, reliable, user-friendly, and efficient operation.

The description herein provides the preferred embodiments of the present invention but should not be construed as limiting the scope of the present air duct sanitizing invention. For example, variations may occur in the overall size of the system control unit housing as long as it remains large enough to contain all of the needed electrical components while also being sufficiently compact for easy installation and efficient use; the size of the optional mounting board for electrical components as long as it can be easily and releasably secured against the back interior wall of the housing; the size and configuration of the fluid reservoir as long as it retains an upper ridge necessary for its support within the keyhole opening through the bottom of the system control unit housing and contains an ample supply of sanitizing fluid to prevent excessive reservoir exchange; the type of material used to construct the housing and its cover as long as they remain lightweight and easily portable; the type of fastening means used between the housing and the cover; the size and type of material used for the fluid pick-up hose which connects the pump to the fluid reservoir; the number of misting nozzles connected to the pump by fluid carrying tubing; the number of misting nozzles connected to each air duct; the configuration and relative positions of the electrical components to one another within the interior of the system control unit housing; the mounting means used for fixing the electrical components securely in their usable positions within the system control unit housing; and the complement of programming features offered by the programmable timer; in addition to other obvious variations not shown or specifically described herein that are also considered without specific reference to be a part of the present invention. Thus, the scope of the present invention should be determined by the appended claims and their legal equivalents, and not limited to the examples given.

DETAILED DESCRIPTION OF PREFERRED EMBODIMENTS

Figure 1:
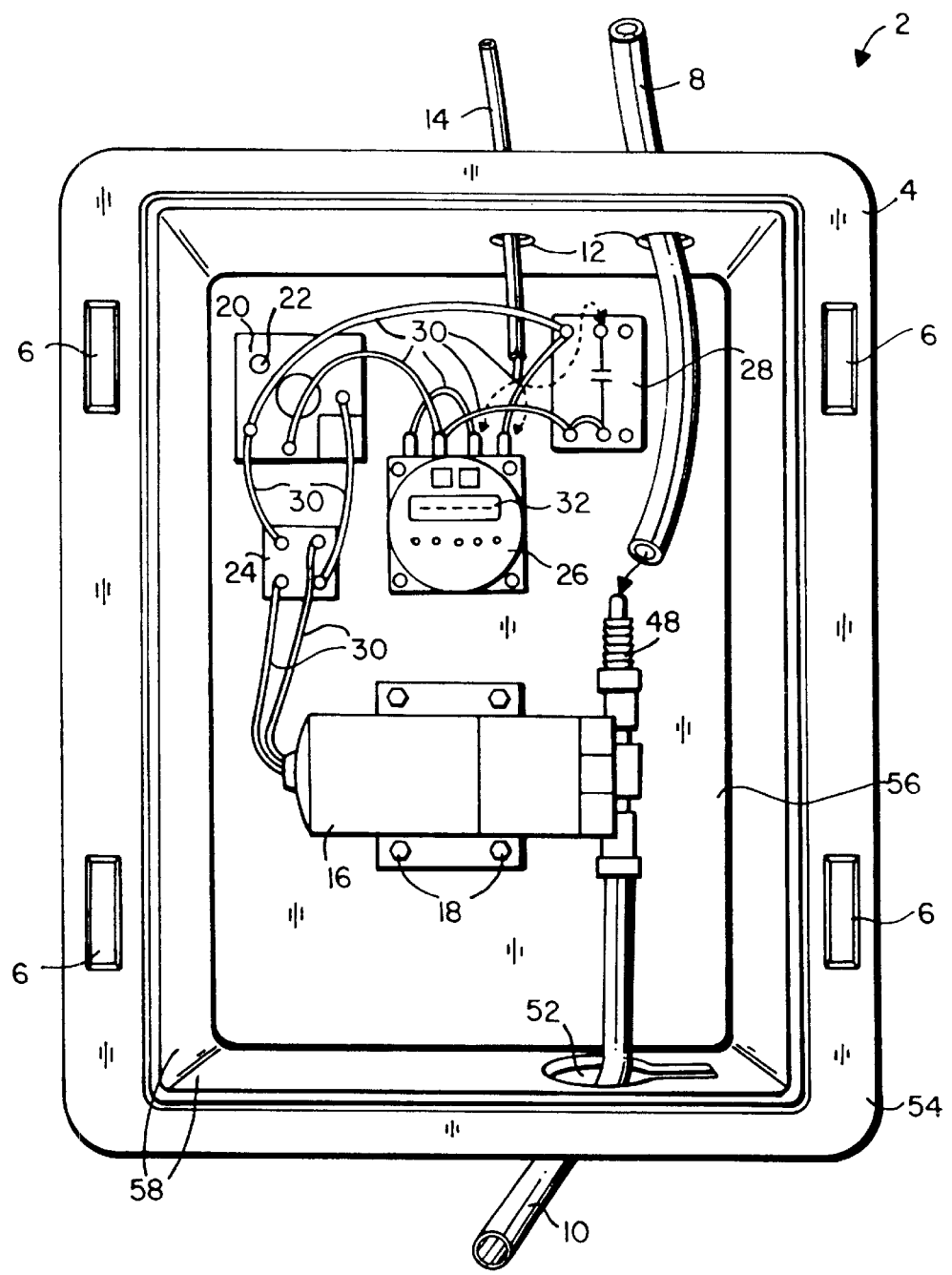
FIG. 1 is a front view of a first preferred embodiment for the system control unit of the present sanitizing system invention, having a compact, portable housing supporting and protecting an electric pump with a barbed hose connection and an attached fluid intake hose, a rectifier, a recycle timer, a programmable timer, and a fan relay electrically wired to cause the pump to periodically draw fluid through the pick-up hose and propel it through the fluid carrying tubing poised for attachment to the barbed hose connection where it ultimately would be emitted from misting nozzles positioned within the branching ends of the fluid carrying tubing that have been inserted through the walls of air ducts, as well as the main plenum to which the ducts are connected, for sanitization purposes to kill molds, mildew, viruses, bacteria, fungi, yeast, algae, and other contaminants within the main plenum and air ducts and maintain them in a sanitized condition.
Figure 3:
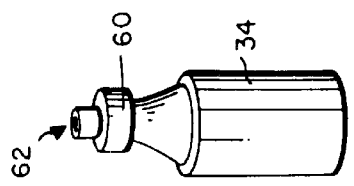
FIG. 3 is an enlarged front view of a preferred embodiment of the fluid reservoir used with the present invention, which has an upper ridge through which it is removably supported during use through a keyhole opening by the bottom wall of the system control unit housing.
Figure 4:
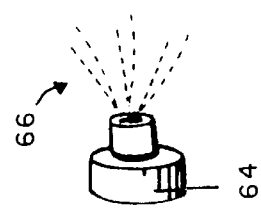
FIG. 4 is an enlarged side view of a preferred embodiment of one of the misting nozzles used with the present invention having a fine mist being discharged therefrom.
Figure 2:
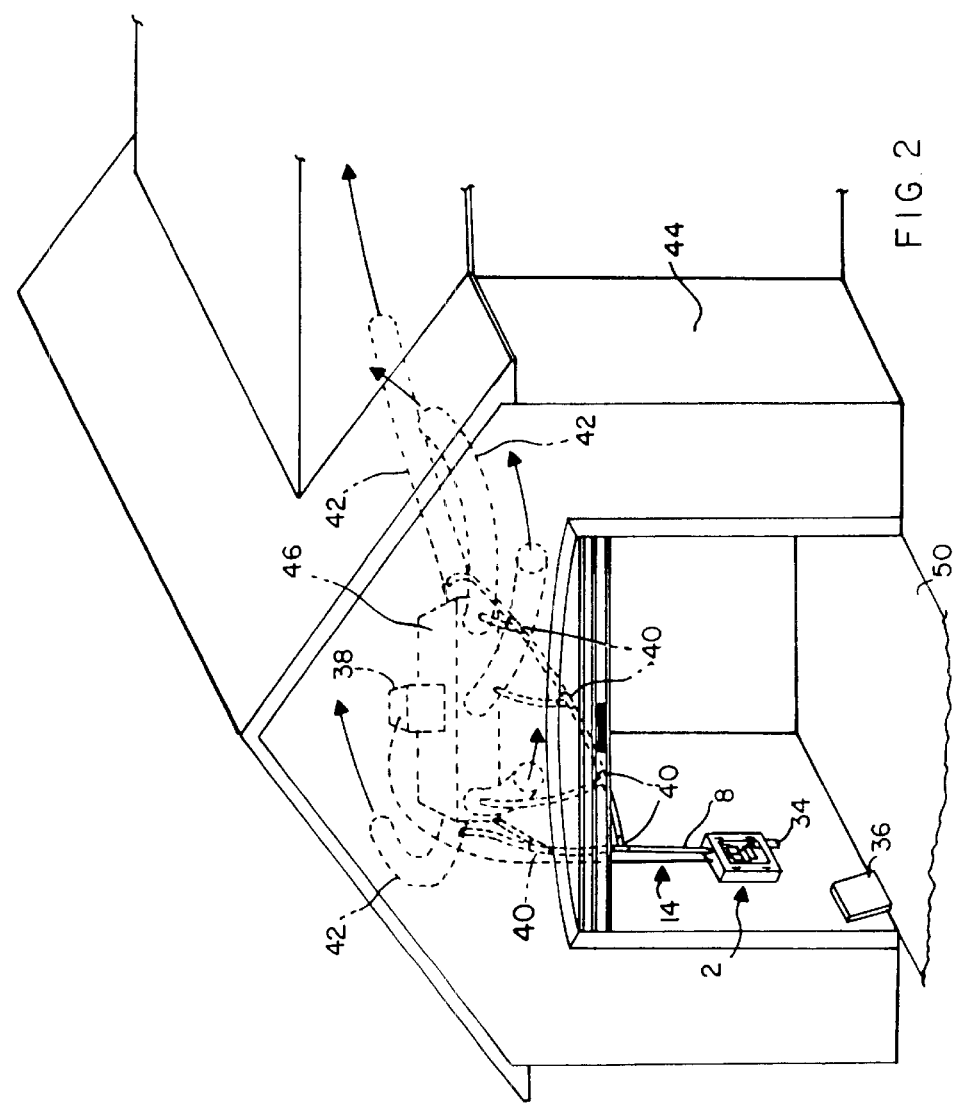
FIG. 2 is a perspective view of the preferred embodiment of the present invention connected to the main plenum, air handler, and air ducts of an air conditioning and heating system in a residential building.
Figure 5:
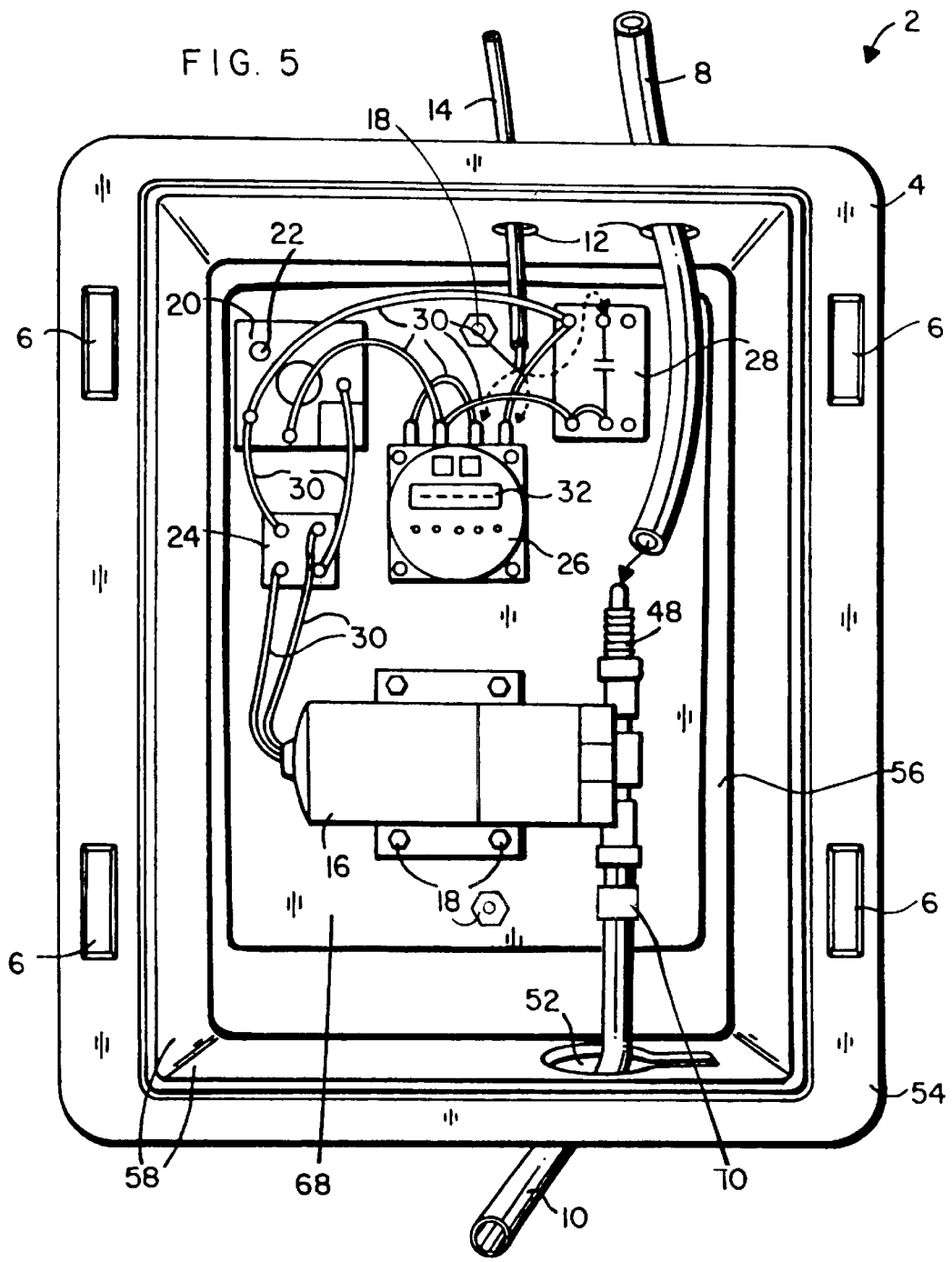
FIG. 5 is a front view of a second preferred embodiment for the system control unit of the present sanitizing system invention having an evaporation prevention cap and wherein its electrical components are attached to a removable planar mounting board that is attached to the inside back wall of the system control unit housing by a minimum number of readily releasable fasteners.

FIGS. 1–5 show the preferred embodiment of an air duct sanitizing system that is sufficiently simple in design to allow a non-professional (not shown) to install and maintain it for a variety of routine uses. FIGS. 1 and 5 show the electrical components of two different preferred embodiments each housed in a pre-assembled system control unit 2, with the electrical components in FIG. 5 being attached to a mounting board removably fixed within the housing 4. FIG. 2 shows system control unit 2 installed on the wall of a garage 50 in a residential building 44, with fluid carrying tubing 8 connecting system control unit 2 to the air ducts 42 and main plenum 46 above garage 50. FIG. 3 shows a preferred embodiment of the non-pressurized refillable fluid reservoir 34 used for storing an available supply of sanitizing agent (not shown) and which is removably supported by the bottom wall 58 of housing 4. FIG. 4 shows a preferred embodiment of one of the misting nozzles 64 used with the present invention, each of which is secured within the distal end of one of the branched segments of fluid carrying tubing 8 and inserted either within the main plenum 46 or within the proximal end of one of the air ducts 42 connected to main plenum 46. The fine mist 66 generated by the misting nozzles 64 is evenly dispersed within main plenum 46 and air ducts 42 to coat their interior surfaces to kill bacteria, viruses, yeast, fungi, algae, molds, and mildew over a period of time and thereafter maintain the interior walls of air ducts 42 and main plenum 46 in a sanitized condition. The fan (not shown) of the associated air conditioning or heating system assists in the dispersal of mist 66, and is activated by fan relay 28 if the fan is not already in an operational mode when the pump begins operation. Although FIG. 2 shows the present invention having only one system control unit 2 in association with residential building 44, should residential building 44 be sufficiently large to need more than one air conditioning or heating zone to control airflow, it is contemplated that additional system control units 2 would be used, with one system control unit 2 and its connected fluid carrying tubing 8 being associated with each zone. Further, use of the present invention is not restricted to residential buildings 44, and although not shown it is considered within the scope of this invention for system control units 2 and fluid carrying tubing 8 to be used with the air conditioning and heating systems in both large and small commercial buildings.

FIG. 1 shows system control unit 2 having a rectangular housing 4 vertically positioned so that its opposed longer walls 58 are vertically oriented and become side walls, and its opposed shorter walls 58 form the top and bottom walls of housing 4. Such orientation, although preferred, is not critical. FIG. 1 shows two substantially round openings 12 through the top wall 58, one for use in extending fluid carrying tubing 8 upwardly beyond housing 4, and the other for use in extending electrical wire 14 upwardly beyond housing 4. The round configuration of openings 12 is preferred but not critical. Further, FIG. 1 shows a keyhole opening 52 through the bottom wall 58 of housing 4, for use in inserting and supporting non-pressurized fluid reservoir 34 during use. As can be seen in FIG. 3, fluid reservoir 34 has a upper ridge 60 that permits fluid reservoir 34 to become suspended within the narrow portion of keyhole opening 52, while the wide portion of keyhole opening 52 allows for easy insertion and removal of the upper ridge 60 through the bottom wall 58 of housing 4. The weight of the liquid sanitizing agent (not shown) within fluid reservoir 34 helps to maintain fluid reservoir 34 securely within the narrow portion of keyhole opening 52 during use. Also, the narrow portion of keyhole opening 52 should have a sufficiently large width dimension to allow easy sliding of fluid reservoir 34 back and forth between the narrow and wide portions of keyhole opening 52. However, the narrow portion of keyhole opening 52 should not have a width dimension that is excessively large relative to the part of fluid reservoir 34 immediately below upper ridge 60 which could allow fluid reservoir 34 to move in response to operational vibration or casual contact toward the wide portion of keyhole opening 52 where it would no longer be properly supported by the bottom wall 58 of housing 4 and potentially in a position to provide less than optimal access by fluid pick-up hose 10 to the sanitizing agent (not shown) within fluid reservoir 34.

In addition to walls 58, FIG. 1 shows housing 4 having an interior back surface 56 and a flange 54 outwardly depending from the front perimeter of walls 58. Although hidden in FIG. 1 by flange 54 and walls 58, it is contemplated for walls 58 to forwardly depend from the perimeter of interior back surface 56. FIG. 1 further shows flange 54 having four spaced-apart rectangular apertures 6, with one rectangular aperture 6 positioned near to each corner of rectangular housing 4 and also positioned adjacent to one of the longer walls 58. It is contemplated for rectangular apertures 6 to be used in providing a snap-fit connection between housing 4 and a cover 36, shown in FIG. 2, that seals tightly against flange 54 to protect the interior of housing 4 from unwanted dirt, dust, debris, and incidental contact. Although not shown, it is contemplated for cover 36 to have a flange similar to flange 54 with four protrusions complementary in configuration for snap-fitting securely into rectangular apertures 6, with each protrusion situated in a position directly opposed to a different one of the rectangular apertures 6. It is contemplated that the snap-fit connection between the rectangular apertures 6 on flange 54 and the opposing protrusions on cover 36 would provide a close connection therebetween, however it should not be so tight as to make it difficult for the person maintaining the present invention to remove cover 36 when service access to the interior of housing 4 is required. It is not contemplated for the removal of cover 36 to be required for the routine change-out and/or refill of fluid reservoirs 34 as they are independently removable through keyhole opening 52. Further, the rectangular configuration of openings 6 is not critical, and they could be round, hexagonal, diamond-shaped or have any other configuration that would allow secure attachment of cover 36 to housing 4. Although not shown, a hinged connection between cover 36 and housing 4 is also considered to within the scope of the present invention, as well as a locking connection between cover 36 and housing 4, or for cover 36 and housing 4 to have a configuration usable with keyed lock, combination lock, or other type of locking device, so that when the present invention is used in commercial buildings, apartment complexes, or other public places, access to the electrical components within housing 4 can optionally be restricted.

FIG. 1 shows housing 4 supporting and protecting an electrical pump 16, a rectifier 24, a recycle timer 20, a fully automated programmable timer 26 with built-in power loss backup, and a fan relay 28. All are directly mounted to the interior back surface 56 of housing 4 and are contemplated for use with 24-volt electrical current. FIG. 1 shows mounting bolts 18 connecting electrical pump 16 to interior back surface 56. Although not shown, when mounting bolts 18 are used, it is also preferred for locking nuts with nylon inserts to be used in securing mounting bolts 18 in place as an anti-vibration precaution. Rubber mounting pads (not shown) could also be positioned between electrical pump 16 and housing 4 as a further anti-vibration precaution. In addition, although the means for attachment to housing 4 is not shown in FIG. 1 for clarity of illustration, and is not critical to the present invention, it is contemplated in the preferred embodiment that rectifier 24, recycle timer 20, programmable timer 26, and fan relay 28 be secured in a fixed position to the plastic interior back surface 56 of housing 4 with a plurality of nuts and mounting bolts 18. FIG. 1 also shows wiring 30 electrically connecting electrical pump 16 to rectifier 24; rectifier 24 to recycle timer 20; recycle timer 20 to programmable timer 26 and fan relay 28; and programmable timer 26 to fan relay 28. Although not limited thereto, in the preferred embodiment shown in FIG. 1, wiring 30 would comprise 16-gauge copper wire. FIG. 1 further shows the end of an electrical wire 14 poised for connection to both the programmable timer 26 and the fan relay 28. Although not shown in FIG. 1, but shown in FIG. 2, the other end of electrical wire 14 would be connected to the air handler 38 of the air conditioning and heating system with which the present invention is associated so that the present invention can draw 24-volt power therefrom for its operation. As a result, no electrical current higher than 24 volts would be connected to housing 4, making the present invention safer for use by non-professional maintenance personnel (not shown).

FIG. 1 also shows electrical pump 16 being connected to a fluid pick-up hose 10 that extends downwardly beyond housing 4 through keyhole opening 52. Fluid pick-up hose 10 is made from flexible tubing material, as shown by its angled configuration in FIG. 1. It is critical that fluid pick-up hose 10 have a length dimension that extends to the bottom of the size of fluid reservoir 34 contemplated for use when it is in a usable position supported by housing 4 through the narrow portion of keyhole opening 52. Also, in the preferred embodiment it is preferred that the outside diameter of fluid pick-up hose 10 be close in dimension to the diameter of top opening 62 in fluid reservoir 34, shown in FIG. 3. However, if the outside diameter of fluid pick-up hose 10 were significantly smaller than the diameter dimension of top opening 62, evaporation of the sanitizing or other liquid stored within fluid reservoir 34 would be likely to occur. To prevent such evaporation, a cap, such as number 70 in FIG. 5, adapted in configuration to closely fit over and/or around top opening 62 can be optionally be mounted on fluid pick-up hose 10 to remain in a position ready for use with a newly refilled or replacement fluid reservoir 34, and an operator would not be required to separately handle such a cap 70, thus keeping operator maintenance simple and minimal. To accommodate fluid reservoirs 34 having different fluid holding capacities, the evaporation preventing cap 70 optionally mounted on fluid pick-up hose 10 could be made minimally slidable along fluid pick-up hose 10 so that it could always be adjusted for optimal positioning over the top opening 62 of every size of fluid reservoir 34 contemplated for use. In a position opposed to fluid pick-up hose 10 and also connected to electrical pump 16, FIG. 1 shows a barbed hose fitting 48 with the one end of a fluid carrying tubing 8 poised for connection thereto. FIG. 1 shows the outer surface of barbed hose fitting 48 having a ribbed configuration that allows fluid carrying tubing 8 to be securely connected to barbed hose fitting 48 without the use of clamps or other fastening devices (not shown).

Although a rectangular configuration is preferred for housing 4, it is not critical and housing 4 could also have different configurations including those that are substantially round, oval, or hexagonal, and still be able to effectively perform its support and protective functions, as long as the portion of bottom wall 58 used for the positioning of keyhole opening 52 is sufficiently horizontal in orientation so that fluid reservoir 34 remains securely in place within the narrow portion of keyhole opening 52 during use. Also, and although not critical, in the preferred embodiment it is contemplated for housing 4 to be made from polyethylene for easy maintenance and to have approximate height, width, and depth dimensions respectively of fifteen inches, thirteen inches, and six inches. The lightweight material from which it is made, and its compact size, would make housing 4 readily portable and easily mounted by a non-professional installer to a variety of mounting surfaces (not shown). Since electrical pump 16 is the component positioned within housing 4 with the greatest depth dimension, at a minimum housing 4 must have a depth dimension sufficient for containment of electrical pump 16 while simultaneously allowing adequate room for secure connection of cover 36. Further, the sizes of rectifier 24, recycle timer 20, programmable timer 26, and fan relay 28 relative to one another is not critical, nor is the positioning of rectifier 24, recycle timer 20, programmable timer 26, and fan relay 28 relative to one another within housing 4, as long as the amount of wiring 30 needed for electrical connection therebetween is not significantly increased.

In the most preferred embodiment of the present invention, recycle timer 20 would operate on 24-volt alternating current and cause activation of electrical pump 16. The preferred recycle timer 20 would have a first cycle set to for a period of approximately thirty seconds, with a second cycle that is adjustable between one and thirty seconds. Recycle timer 20 would also have a control 22 for adjusting the duration of the second cycle. The longer the run cycle of electrical pump 16, the more sanitizing agent (not shown) or other liquid in fluid reservoir 34 is drawn through pump 16 and forced through misting nozzles 64. Fan relay 28 would also operate on 24-volt alternating current, and as shown in FIG. 1 by the symbol marked between the two centrally positioned terminals, its circuitry would normally be in an open position. Once electricity is directed to fan relay 28, the circuit would close to cause by-passing of a thermostat in the air conditioning or heating system with which the present invention is associated when the fan is not in an operating made at the beginning of pump operation. The resulting activation of the air conditioning or heating system fan would then create even dispersal within the main plenum 46 and air ducts 42, shown in FIG. 2, of the 250μ or smaller droplets in the mist 66 formed by misting nozzles 64 positioned at the distal ends of various branched segments of fluid carrying tubing 8. Programmable timer 26 would operate on 24-volt alternating current, however, it would have a backup provision for power loss protection so that reprogramming is not necessary every time the power drawn from the associated air conditioning or heating system fails for a short period of time. The preferred programmable timer 26 would also have a capacitor power loss backup, an internal clock (not shown), a by-pass mode, a control for instantaneous system activation, and a digital display 32 for programming assistance. Since it is contemplated that electrical pump 16 would operate on 24-volt direct current instead of 24-volt alternating current, it is contemplated for electrical pump 16 to be connected to a full bridge rectifier 24 that changes 24-volt alternating current into 24-volt direct current. Further, electrical pump 16 would operate to force sanitizing, air purification, or aromatherapy liquid (not shown) into fluid carrying tubing 8 at approximately 60 psi, have the ability to operate safely even though no liquid is available in fluid reservoir 34, and have an internal by-pass loop for pumped liquid should the discharge opening within barbed hose connection 48 in electrical pump 16 become blocked or inoperative for any reason. Further, misting nozzles 64 would be made from stainless steel encased in brass so that they would never become clogged and never wear out, another feature incorporated into the present invention to reduce operator maintenance and expense.

FIG. 5 shows a second preferred embodiment of system control unit 2, similar to FIG. 1, with the addition of a planar mounting board 68 to which all electrical components within housing 4 are attached and an evaporation prevention cap 70 attached to fluid pick-up hose 10. FIG. 5 also shows two inverted mounting bolts 18 used for readily releasable attachment of mounting board 68 to the interior back surface 56 of housing 4. The size of mounting board 68 is not critical as long as all electrical components selected for placement within housing 4 can be attached thereto without overcrowding. Therefore, the perimeter dimension of mounting board 68 may be only slightly smaller than the perimeter dimension of the back surface of housing 4, or the perimeter dimension of mounting board 68 may be substantially less than the perimeter dimension of the back surface of housing 4, as shown in FIG. 5. Also, the mounting bolts 18 used to affix mounting board 58 to interior back surface 56 are inverted so that mounting board 58 can be removed from housing 4 without detaching housing 4 from its support surface (not shown). Since the nuts securing mounting bolts 18 are positioned within housing 4, they are readily accessible for prompt counter-rotation and removal from mounting inverted mounting bolts 18, paving the way for subsequent separation of mounting board 58 from inverted mounting bolts 18 and ultimate disconnection from housing 4. The configuration of nut used to secure mounting bolts 18 in place is not critical as long as the nuts are readily releasable from mounting bolts 18. Although not illustrated, since winged nuts are easily and readily hand-manipulated, they are also considered within the scope of the present invention for such purpose. While the number of inverted mounting bolts 18 is not critical, a small number is contemplated, and two such inverted mounting bolts 18 are considered adequate for most purposes.

FIG. 2 shows system control unit 2 mounted on the wall of a garage 50 in a residential building 44. In such a position, system control unit 2 is conveniently located for easy maintenance access. Should more than one system control unit 2 be used in residential building 44 to service different air circulation zones, the multiple system control units 2 can be consolidated in location for efficient operator maintenance, or easily mounted apart from one another depending upon the space available or other such need. FIG. 2 shows the lower part of fluid reservoir 34 extending below the bottom wall 58 of system control unit 2, with fluid reservoir 34 illustrated as being connected to and supported by system control unit 2. FIG. 2 also shows cover 36 separated from system control unit 2 and leaning against a wall in garage 50 in an out-of-the-way position until it is again needed for use in protecting the interior of system control unit 2 from unwanted dust, dirt, debris, and inadvertent contact. The air conditioning and heating system servicing residential building 44 sits above garage 50 and is shown to include main plenum 46, air handler 38 positioned adjacent to main plenum 46, and five air ducts 42 each connected on one of its ends to main plenum 46. The arrows in FIG. 2, which extend beyond each air duct 42, show the direction of airflow within air ducts 42. FIG. 2 further shows an electrical wire 14 extending upwardly beyond the upper wall 58 of system control unit 2 and being connected on its upper end to air handler 38. It is through electrical wire 14 that the present invention obtains the reduced voltage current needed to operate electrical pump 16, rectifier 24, recycle timer 20, programmable timer 26, and fan relay 28, and enhance operator safety. Fluid carrying tubing 8 also extends upwardly beyond the upper wall 58 of system control unit 2 where through the use of several T-shaped barbed hose connectors 40 it becomes a branched array that provides fluid communication between system control unit 2 and main plenum 46, as well as each air duct 42 connected to main plenum 46. The multiple connections of fluid carrying tubing 8 into all of the air ducts 42 connected to main plenum 46 provides for more even distribution of the sanitizing agent mist, shown in FIG. 4 by the number 66, within air ducts 42 so that air ducts 42 remain in a sanitized condition once the initial treatment period of approximately 30 days is complete. Connection of fluid carrying tubing 8 to each air duct 42 is easily accomplished. A pilot hole (not shown) is made into each air duct 42 close to main plenum 46. Thereafter, sealant (not shown) is used to secure each branching segment of fluid carrying tubing 8 within a different one of the pilot holes made. Although not generally required, it is considered within the scope of the present invention for more than one misting nozzle 64 and segment of fluid carrying tubing 8 to be connected to each available air duct 42. Thus the present invention can be effectively used in new construction, as well as easily provide unlimited retrofit capability to different types of existing air conditioning and heating systems. The size, type, location, and orientation of main plenum 46, air handler 38, and air ducts 42 are not an impediment to connection and use of the present invention therewith. Thus even when the main plenum 46 is oriented in a horizontal position in an attic, or in a vertical position within a garage or a closet, use of the present invention is easily accomplished.

FIG. 3 shows a preferred embodiment of fluid reservoir 34, which can be used to store an available quantity of liquid air duct sanitizing agent (not shown), or in the alternative air purification and aromatherapy fluids. Fluid reservoir 34 is not pressurized and although not clearly shown in FIG. 3, it has a top opening 62 through which fluid pick-up hose 10 is inserted during use. The size and configuration of fluid reservoir 34 are not critical, although the quantity of sanitizing fluid (not shown) made available must be adequate to keep operator maintenance to a minimum. Only a small amount of sanitizing fluid is drawn from fluid reservoir 34 during each cycle of electric pump 16. Therefore, even if electric pump 16 is activated six times in a day, a fluid reservoir 34 having a quart capacity would be adequate for most uses. Although not shown and not limited thereto, the preferred chemical used with the present invention for air duct sanitizing purposes is chlorine dioxide, which is approved by the U.S. Environmental Protection Agency for such use. It has a low toxicity, a category III EPA safety rating, and kills bacteria, viruses, fungi, yeast, algae, molds, and mildew. Also, there is no special handling or disposal required for empty fluid reservoirs 34 which are discarded or recycled. Further, chlorine dioxide provides point-of-contact microbial control and there is no activation or rinsing required. For air purification purposes, a chemical such as OXINE can be used, however buildings so treated must be unoccupied. Once a building requiring air purification treatment has been vacated, a quart of appropriate chemical will be added to reservoir 34. Programmable timer 26 will be set to allow electrical pump 16 to run continuously for a period of approximately one hour, after which occupants will be allowed to return to the treated building following an additional cure period of approximately one hour to allow the chemical to dissipate to safe levels. Although not shown, aromatherapy can be accomplished by either adding a pleasing scent to air sanitizing chemicals, or independently placing aromatherapy solutions in fluid reservoir 34 and adjusting progranmmable timer 26 to distribute appropriate quantities of the aromatherapy chemicals into the building atmosphere to achieve a pleasing effect. It is critical that the fluid pick-up hose 10 for insertion within top opening 62 in fluid reservoir 34 has a length dimension that extends to the bottom of the largest size of fluid reservoir 34 contemplated for use, when it is in its usable position supported by housing 4 through the narrow portion of keyhole opening 52, so that the full amount of sanitizing agent or other liquid stored in fluid reservoir 34 is available for use. Also, in the preferred embodiment it is preferred that the outside diameter of fluid pick-up hose 10 be close in dimension to the diameter of top opening 62 in fluid reservoir 34 to prevent evaporation of the sanitizing agent or other liquid stored within fluid reservoir 34. If the diameter dimension of fluid pick-up hose 10 is significantly smaller than the diameter of top opening 62, an evaporation-preventing cap (not shown) should be used that is adapted in configuration to closely fit over and/or around top opening 62. To keep operator maintenance simple and minimal, such a cap can be mounted on fluid pick-up hose 10 so that it would remain in a position ready for use with a newly refilled or replacement fluid reservoir 34. Also, to accommodate reservoirs 34 having different fluid holding capacities, the evaporation-preventing cap mounted on fluid pick-up hose 10 could be optionally made minimally slidable along fluid pick-up hose 10 so that it could always be adjusted for optimal positioning over the top opening 62 of every size of fluid reservoir 34 used.

FIG. 4 is an enlarged side view of a preferred embodiment of one of the misting nozzles 64 used with the present invention for emitting a fine mist 66 of sanitizing, air purification, or aromatherapy chemicals. The exact configuration of misting nozzle 64 is not critical, and it is considered within the scope of the present invention to have misting nozzles 64 which have other sizes and shapes as long as they are relatively lightweight and capable of producing a fine mist of droplets having a maximum diameter of approximately $250\mu$. It is contemplated that each misting nozzle 64 used with the present invention be made from stainless steel wrapped in brass to minimize maintenance cost since it would resist clogging and never wear out. Also, although not shown, a hose fitting connection can be used to securely attach each misting nozzle 64 into the end of one branching segment of fluid carrying tubing 8 so that the misting nozzle 64 can be readily seated within an air duct 42 to spray a fine mist 66 of droplets having a maximum diameter dimension of approximately $250\mu$ to kill undesired organisms within the interior of air duct 42, such as bacteria, viruses, algae, fungi, yeast, molds, and mildew.

To use the present invention an operator (not shown) would assemble one segment of 200 psi rated fluid carrying tubing 8 to other similar segments with T-shaped barbed hose connections 40 to form a branched array of fluid carrying tubing 8. One such segment would be provided for each misting nozzle 64 needed for use. The trunk line of the branching array would be connected to the barbed hose fitting 48 surrounding the discharge opening of electrical pump 16. Each misting nozzle 64 would be secured within one of the ends of a different one of the fluid carrying tubing 8 segments. Although one misting nozzle 64 is usually adequate to sanitize an air duct 42, it is considered within the scope of the present invention for more than one misting nozzle 64 to be used in an air duct 42. Therefore, at least one pilot hole (not shown) would be formed through each air duct 42 targeted for sanitization and one or more pilot holes would be formed through the main plenum 46 to which the air ducts 42 are attached. The pilot holes in the air ducts 42 would be located near to main plenum 46. After the pilot holes are made, a quantity of sealant (not shown) is used to secure each misting nozzle 64 within the main plenum or a different one of the air ducts 42 so that each pilot hole is filled with a misting nozzle 64 secured within a segment of fluid carrying tubing 8. The system control unit 2 of the present invention would be mounted within the building targeted for sanitization, such as residential building 44, in a place easily accessible for operator maintenance. Preferably, once system control unit 2 is secured into its usable position, an electrical wire 14 would be connected between the air handler 38 of the air conditioning or heating system with which the present invention is associated and programmable timer 26, as well as fan relay 28. A fluid reservoir 34 with the type and quantity of sanitizing, air purification, or aromatherapy liquid appropriate to the intended application would then be selected and connected to system control unit 2 by inserting fluid pick-up hose 10 through top opening 62 in fluid reservoir 34, and also inserting fluid reservoir 34 through the larger portion of keyhole opening 52 in bottom wall 58 of housing 4 and sliding fluid reservoir 34 into the narrow portion of keyhole opening 52 to lock fluid reservoir 34 into its usable position with upper ridge 60 supported by the inside surface of bottom wall 58. To exchange an empty fluid reservoir 34 for a full one, or to refill it, the operator would not have to remove cover 36 from housing 4, and instead only need to slide fluid reservoir 34 from the narrow portion of keyhole opening 52 toward the larger portion of keyhole opening 52, followed by the application of a downward force to the bottom part of fluid reservoir 34 sufficient to cause upper ridge 60 and top opening 62 to become withdrawn from the larger portion of keyhole opening 52. Safety features for the operator (not shown) include the high-pressure fluid carrying tubing 8 rated three times that encountered during normal operation of electrical pump 16, the reduced voltage programmable timer 26 and electrical pump 16 to reduce the potential risk of fire and operator injury since fluid and electricity are used together within housing 4, an electrical pump 16 that safely operates wet or dry should the operator fail to anticipate timely replacement or refill of fluid reservoir 34 before all of the liquid (not shown) therein is completely used, and the non-pressurized supply of sanitizing agent or other liquid provided for use. The present invention is also user-friendly in many ways. Housing 4 can be mounted anywhere that is convenient for maintenance access, and it is not needed to position housing 4 close to the main plenum 46, any air duct 42, or an electrical outlet (not shown). Also, it is contemplated for housing 4 to be made from plastic materials that are essentially maintenance-free and resistant to deterioration by the corrosive chemicals sometimes used for air sanitization. The plastic material also makes housing 4 lightweight and easily portable during installation. In addition, cover 36 is designed for easy separation from housing 4 when operator entry into the interior of housing 4 is required. Also, the optional use of a mounting board 68 to attach electrical pump 16, programmable timer 26, fan relay 28, rectifier 24, and recycle timer 20 to housing 4 facilitates manufacture and benefits the owner and/or operator by allowing the removal only of the mounting board 68, and not the entire housing 4, for assessment of maintenance needs in the event of component failure. Further, the type, orientation, and location of main plenum 46 have no adverse impact on the installation of the present invention, as the present invention is simple in design and widely adaptable for retrofitting to existing air conditioning and heating systems.

What is claimed is:

1. A user-friendly, portable air duct conditioning apparatus, for new construction and retrofitting to existing air conditioning and heating systems having an air handler, a fan, a thermostat, and a main plenum with several connected air ducts, which can be easily installed and routinely serviced by a homeowner or other non-professional, said apparatus comprising:

a compact control unit housing having a hollow interior, cover means adapted for safeguarding said hollow interior and ready user access to said hollow interior, and a bottom surface with an opening therethrough;

a reservoir of liquid air conditioning agent having a closed bottom and an open top with a configuration adapted for temporary support of said reservoir within said bottom surface opening of said housing in a position that allows for said open top to be placed securely within said hollow interior during use and also allows for said open top to be easily and promptly removable from said bottom surface opening of said housing when replacement of said liquid air conditioning agent is required;

a low voltage electric pump securely fixed within said hollow interior of said housing said pump having a discharge opening, being adapted for propelling said liquid air conditioning agent at a minimum pressure of approximately 60 psi through said discharge opening, and having a fluid bypass loop;

a fluid pick-up hose connected between said reservoir and said pump, said fluid pick-up hose having a distal end positioned adjacent to said bottom surface of said reservoir so that substantially all of said liquid air conditioning agent in said reservoir can be drawn therefrom by said pump;

a low voltage fully automated programmable timer with power loss backup means, said timer being securely fixed within said hollow interior of said housing;

at least one misting nozzle in fluid communication with the main plenum and at least one misting nozzle in fluid communication with each air duct connected to the main plenum, each said nozzle being adapted to create a mist having a droplet size of less than approximately 250 $\mu$;

a quantity of fluid carrying tubing adapted for connection between said pump and each said nozzle, said tubing being adapted for transporting liquids at pressures exceeding 60 psi;

electrical connection means connected between said timer and the air handler of the associated air conditioning system, said electrical connection means being adapted for providing low voltage power to said timer and said pump;

low voltage fan bypass relay means also connected to the air handler by said electrical connection means, said fan bypass relay means being adapted for bypassing the air conditioning system thermostat and activating the air conditioning system fan if it is not already functioning when operation of said pump begins, said fan bypass relay also being securely fixed within said hollow interior of said housing;

a recycle timer securely fixed within said hollow interior of said housing;

attachment means adapted to secure said pump, said programmable timer, said recycle timer, and said fan bypass relay within said housing; and a quantity of electrical wiring, said wiring being adapted for low voltage connection of said recycle timer to said programmable timer, said recycle timer to said fan relay, said recycle timer to said pump, and said programmable timer to said fan relay whereby said control unit housing is mounted in a remote position from the air ducts and the main plenum that is easily accessed for maintenance and servicing purposes, said programmable timer will periodically activate said pump to draw metered quantities of said liquid air conditioning agent from said reservoir and propel said liquid air conditioning agent through said fluid carrying tubing to each said misting nozzle wherein a fine mist of droplets is created from said liquid air conditioning agent that becomes evenly dispersed through the air ducts and the main plenum of the air conditioning system by its fan.

2. The apparatus of claim 1 wherein said pump, said programmable timer, said recycle timer, and said fan bypass relay all operate on 24-volt current.

3. The apparatus of claim 1 wherein said air conditioning fluid is selected from a group consisting of rinse-free point-of-contact microbial control air sanitizing agents adapted to kill bacteria, viruses, yeasts, fungi, algae, molds, and mildew air purification agents, air de-odorizing agents, chlorine dioxide, OXINE, and aromatherapy agents.

4. The apparatus of claim 1 further comprising an evaporation prevention cap connected to said fluid pick-up hose and adapted for blocking evaporation of said liquid air conditioning agent positioned within said reservoir, and wherein said power loss backup means comprises a capacitor, said electrical connection means comprises an elongated electrical wire, said reservoir configuration comprises an upper ridge, and said bottom surface opening in said housing further comprises a keyhole configuration adapted for support of said upper ridge.

5. The apparatus of claim 1 further comprising a full bridge rectifier adapted to convert 120-volt alternating current into 24-volt direct current, wherein said pump is adapted to operate on 24-volt direct current, and wherein said quantity of electrical wiring connects said pump to said rectifier and said rectifier to said recycle timer.

6. The apparatus of claim 1 wherein said attachment means comprises a plurality of nuts and mounting bolts, and said cover means is selected from a group consisting of removable covers and hinged covers.

7. The apparatus of claim 1 wherein said fluid carrying tubing has a minimum pressure rating of approximately 200 psi.

8. The apparatus of claim 1 wherein said housing comprises polyethylene and each said misting nozzle comprises stainless steel and brass.

9. The apparatus of claim 1 further comprising a planar mounting board, said mounting board is releasably fastened to said housing, and wherein said programmable time, said pump said fan bypass relay, and said recycle timer are all connected to said mounting board.

10. The apparatus of claim 1 wherein said pump is configured to continue operation even when said all of said liquid air conditioning agent is removed from said reservoir.

11. A user-friendly, portable air duct conditioning apparatus, for new construction and retrofitting to existing air conditioning and heating systems having, an air handler, a fan, a thermostat, and a main plenum with several connected air ducts, which can be easily installed and routinely serviced by a homeowner or other non-professional, said apparatus comprising:

a control unit housing having a hollow interior, a cover configured for safeguarding said hollow interior and ready user access to said hollow interior, and a bottom surface with an opening therethrough;

a reservoir of liquid air conditioning agent having a closed bottom and an open top with a configuration adapted for temporary support of said reservoir by said bottom surface opening of said housing in a position that allows for said open top to be placed securely within said hollow interior during use and also allows for said open top to be easily and promptly removable from said bottom surface opening of said housing when replacement of said liquid air conditioning agent is required;

a 24-volt direct current electric pump securely fixed within said hollow interior of said housing, said pump having a discharge opening, being adapted for propelling said liquid air conditioning agent at a minimum pressure of approximately 60 psi through said discharge opening, and having a fluid bypass loop;

a fluid pick-up hose connected between said reservoir and said pump, said fluid pick-up hose having a distal end positioned in close proximity to said bottom surface of said reservoir so that substantially all of said liquid air conditioning agent in said reservoir can be drawn therefrom by said pump;

a 24-volt alternating current fully automated programmable timer with power loss backup, said timer being securely fixed within said hollow interior of said housing;

at least one misting nozzle in communication with the main plenum and at least one misting nozzle in fluid communication with each air duct connected to the main plenum, each said nozzle being adapted to create a mist having a droplet size of less than approximately 250 $\mu$;

a quantity of fluid carrying tubing configured to propel fluids at a maximum pressure of approximately 200 psi and connection between said pump and each said nozzle;

electrical connection means connected between said programmable timer and the air handler of the associated air conditioning system, said electrical connection means being adapted for providing 24-volt power to said timer and said pump, and comprising a full bridge rectifier adapted to convert 24-volt alternating current into 24-volt direct current, said rectifier securely fixed within said housing; a 24-volt alternating current fan bypass relay also connected by said electrical connection means to the air handler, said fan bypass relay being configured for bypassing the air conditioning system thermostat and activating the air conditioning system fan if it is not already functioning when operation of said pump begins, said fan bypass relay also being securely fixed within said hollow interior of said housing;

a 24-volt alternating current recycle timer securely fixed within said hollow interior of said housing;

attachment means adapted to secure said pump, said programmable timer, said recycle timer, said rectifier, and said fan bypass relay within said housing; and a quantity of electrical wiring, said wiring being adapted for connection of said recycle timer to said programmable timer, said recycle timer to said fan relay, said recycle timer to said rectifier, said rectifier to said pump, and said programmable timer to said fan relay whereby when said housing is mounted in a remote position from the air ducts and the main plenum that is easily accessed for maintenance and servicing purposes, said programmable timer will periodically activate said pump to draw metered quantities of said liquid air conditioning agent from said fluid reservoir and propel said liquid air conditioning agent through said fluid carrying tubing to each said misting nozzle wherein a fine mist of droplets is created from said liquid air conditioning agent that becomes evenly dispersed through the air ducts and the main plenum of the air conditioning system by its fan.

12. The apparatus of claim 11 wherein said air conditioning fluid is selected from a group consisting of rinse-free point-of-contact microbial control air sanitizing agents adapted to kill bacteria, viruses, yeasts, fungi, algae, molds, and mildew, air purification agents, air de-odorizing agents, chlorine dioxide, OXINE, and aromatherapy agents.

13. The apparatus of claim 11 further comprising an evaporation prevention cap connected to said fluid pick-up hose and adapted for blocking evaporation of said liquid air conditioning agent positioned within said reservoir, and wherein said power loss backup means comprises a capacitor, said electrical connection means comprises an elongated electrical wire, said reservoir configuration comprises an upper ridge, said housing further comprises a keyhole opening adapted for support of said upper ridge, and said means of ready access to said housing interior is selected from a group consisting of removable covers and hinged covers.

14. The apparatus of claim 11 wherein said housing is compact in configuration and comprises polyethylene, said pump is adapted to operate wet or dry, said pump also is configurea to have a fluid bypass loop for optional circulation of said air conditioning fluid in lieu of said fluid being propelled from said discharge opening, and each said misting nozzle comprises stainless steel and brass.

15. The apparatus of claim 11 further comprising a planar mounting board, said mounting board is releasably fastened to housing, and wherein said programmable time, said pump, said fan bypass relay, said rectifier, and said recycle timer are all connected to said mounting board.

* * * * *